United States Patent [19]

Suzuki et al.

[11] Patent Number: 4,993,480
[45] Date of Patent: Feb. 19, 1991

[54] TEMPERATURE CONTROLLING MEANS FOR A THERMOSTAT FOR USE IN MEASURING VISCOSITY

[75] Inventors: Osamu Suzuki, Kumagaya; Syousuke Ishiwata, Yoriimachi; Mitsuroh Hayashi; Hideaki Oshima, both of Kumagaya, all of Japan

[73] Assignee: Chichibu Cement Kabushiki Kaisha, Japan

[21] Appl. No.: 440,402

[22] Filed: Nov. 17, 1989

Related U.S. Application Data

[63] Continuation-in-part of Ser. No. 305,299, Feb. 1, 1989, abandoned.

[51] Int. Cl.$^5$ ............................................. F25B 29/00
[52] U.S. Cl. ........................................... 165/2; 165/27; 165/30; 165/32; 165/61; 236/78 D; 236/15 BB; 364/137; 364/162; 364/557
[58] Field of Search .................. 165/2, 27, 30, 32, 61; 364/557, 162, 137; 62/201; 236/78 D, 15 BB

[56] References Cited

U.S. PATENT DOCUMENTS

| | | | |
|---|---|---|---|
| 2,876,327 | 3/1959 | Leisey | 165/32 |
| 3,770,946 | 11/1973 | Fertik | 364/162 |
| 3,824,479 | 7/1974 | Alger | 364/162 |
| 4,214,300 | 7/1980 | Barlow et al. | 364/162 |
| 4,232,364 | 11/1980 | Bibbero | 364/162 |
| 4,368,510 | 1/1983 | Anderson | 364/162 |
| 4,407,013 | 9/1983 | Arcara et al. | 364/162 |
| 4,734,872 | 3/1988 | Eager et al. | 364/557 |

FOREIGN PATENT DOCUMENTS

| | | | |
|---|---|---|---|
| 0094104 | 5/1986 | Japan | 364/162 |
| 0128303 | 6/1986 | Japan | 364/162 |
| 0160102 | 7/1986 | Japan | 364/162 |

OTHER PUBLICATIONS

Fishbeck, James, "Writing P-I-D Control Loops Easily in Basic", Control Engineering, vol. 25, No. 10, pp.45–47, Oct. 1978.
Kawata, Michio, "Viscosity", Revised Edition published by Corona Co., Jul. 1983, pp. 32, 41, 106, 109–110.

Primary Examiner—John Ford
Attorney, Agent, or Firm—Bruce L. Adams; Van C. Wilks

[57] ABSTRACT

Temperature controlling means for a thermostat for use in viscosity measurement including: a first thermometer detecting the temperature of a fluid sample which is immersed in a thermostat and whose viscosity is measured; a first controller obtaining the difference between a desired set point and the detected value of the sample temperature, momently calculating a set point of temperature of the thermostat according to an operation formula expressed as a function of the above temperature difference and making a controlled signal corresponding to the calculated set point; a second thermometer detecting the temperature of the thermostat; a heating and cooling device for heating and cooling a medium bath of the thermostat; and a second controller making a controlled signal for operating the heating and cooling device under a PID control formed on the basis of the difference between the calculated set point and the detected value of the thermostat temperature and inputting the PID controlled signal into the heating and cooling device.

26 Claims, 7 Drawing Sheets

TEMPERATURE CONTROLLING MEANS FOR A THERMOSTAT FOR USE IN MEASURING VISCOSITY

This is a continuation-in-part of parent application Ser. No. 305,299 filed Feb. 1, 1989 now abandoned.

FIELD OF THE INVENTION

The present invention relates to temperature controlling means for a thermostat, and more particularly but not exclusively to temperature controlling means by which, in measuring the viscosity of a fluid sample immersed in a bath of the thermostat, the temperatures of the bath and the fluid sample are effectively controlled over a wide temperature range.

BACKGROUND OF THE INVENTION

In measuring the viscosity of a fluid sample, the temperature of the fluid sample is generally controlled by using a thermostat. Water, oil or the like are used as a liquid for heating and cooling the fluid sample, and the temperature of the fluid sample is indirectly controlled through regulation of the temperature of liquid. Therefore, it requires a lot of time to adjust the fluid sample temperature to a desired set point. In addition, when the viscosity of the fluid sample is sequentially measured over a wide temperature range, it may be difficult to estimate the actual temperature of the sample varying with time after changing the set point of the fluid sample temperature.

For example, as described in Kawata, Michio; Viscosity, Revised Edition; Corona Publishing Co., Ltd., Japan; 1983; page 41, in a capillary viscometer, the viscometer is immersed in a liquid bath of a thermostat, and the temperature of the liquid bath is regarded as the temperature of a fluid sample within the viscometer. However, because the temperature of the sample cannot be directly measured in addition to the fact that the heat conductivity of the sample differs with the kind of sample, it takes a long time to correctly determine a relationship between viscosity and temperature of the sample.

Also, as described on pages 109 to 110 of the above technical book, in a rotation viscometer, a sample container is surrounded by a water jacket, and water is forcedly circulated between the jacket and a water bath of a thermostat installed outside the jacket to control the temperature of the sample. In this case, temperature controlling is carried out with respect to the water in the thermostat without feedback of the temperature of the sample to the temperature controlling of the thermostat. It is, therefore, not easy to adjust the sample temperature to a desired set point.

SUMMARY OF THE INVENTION

It is an object of the present invention to remove these drawbacks as noted above with respect to prior art.

The present inventors have previously invented a novel tuning fork vibration-type viscometer and have disclosed it in Japanese Laid-Open patent application Ser. No. 107236/1984 and U.S. Pat. No. 4,729,237 issued Mar. 8, 1988. Particularly stimulated by a desire to precisely speedily control the temperature of a fluid sample whose viscosity is to be measured in using such a novel viscometer, the inventors have accomplished the present invention.

The present invention provides temperature controlling means wherein, in measuring the viscosity of a fluid sample, the temperature of the fluid sample is detected and the detected temperature is fed back to temperature controlling means of a thermostat and the temperature of the thermostat is subjected to a PID (proportional-+integral+differential) control.

In accordance with the present invention, the temperature of the fluid sample can be effectively speedily adjusted to any desired set point in a wide temperature range.

According to one aspect of the present invention, there is provided a temperature controlling means of the present comprising:

first means for detecting the temperature of a fluid sample immersed in a liquid bath of a thermostat and making a first output signal corresponding to the detected temperature of the fluid sample;

a first controller for receiving the first output signal from the first thermometer and an input command corresponding to a desired set point of temperature of the fluid sample and determining a set point of temperature of the fluid sample and determining a set point of temperature of the liquid bath according to one if first and second operation formulas expressed as a function of the difference between the desired set point temperature of the fluid sample and its detected temperature and making one of first and second controlled signals corresponding to the respective liquid bath set point temperatures determined by carrying out the first operation formula and the second operation formula;

second means for checking the difference between the set point temperature of the fluid sample and its detected temperature whether or not the absolute value of the difference exceeds a predetermined value of temperature and performing the first operation formula when the absolute value exceeds the predetermined value and performing the second operation formula when the absolute value is at most equal to the predetermined value;

third means for limiting either of the levels of the first and second controlled signals relative to the level of the input comand corresponding to the fluid sample set point temperature, the fourth means being operative to determine a temperature error by subtracting the fluid sample set point temperature from the determined set point temperature of the liquid bath, to check the temperature error whether or not the absolute value of the temperature error exceeds a given value of temperature and to set the new value of the liquid bath set point temperature equal to the sum of the fluid sample set point temperature and the given value when the temperature error exceeds the given value and equal to the value of the fluid sample set point temperature minus the given value when the temperature error is less than the negative quantity of the given value;

fourth means for detecting the temperature of the liquid bath and making a second output signal corresponding to the detected temperature of the liquid bath;

heating and cooling means for heating and cooling the medium bath; and a second controller for receiving the second output signal and one of the first and second controlled signals the levels of which have been limited by the third means, forming an actuating signal corresponding to the difference in level between received one of the first and second controlled signals and the second output signal and subsequently inputting a PID controlled signal formed on the basis of the actuating signal to the heating and cooling means.

According to another aspect of the invention, there is provided a method of controlling the temperature of a fluid sample inmmersed in a liquid bath, comprising the steps of:

A method of controlling the temperature of a fluid sample immersed in a liquid bath, comprising the steps of (a) measuring the temperature of the fluid sample;
(b) determining the fluid sample temperature difference between a desired set point temperature of the fluid sample and its measured temperature;
(c) determining a set point temperature of the liquid bath according to one of first and second operation formulas expressed as a function of the fluid sample temperature difference, the first and second operation formulas being carried out when the absolute value of the fluid sample temperature difference exceeds a predetermined value of temperature and when said absolute value is within the predetermined value, respectively;
(d) determining the set point temperature difference between the determined set point temperature of the liquid bath and the set point temperature of the fluid sample;
(e) setting the new value of the set point temperature of the liquid bath equal to the sum of the fluid sample set point temperature and a given value of temperature when the set point temperature difference is more than the given value, and equal to the value of the fluid sample set point temperature minus the given value when the set point temperature difference is less than the negative quantity of the given value;
(f) measuring the temperature of the liquid bath;
(g) determining the liquid bath temperature difference between the set point temperature of the liquid bath and its measured temperature, where the value of the liquid bath set point temperature is equal to the one determined in the step (c) when the absolute value of the set point temperature difference is within the given value and is equal to one of the new values set in the step (e) when said absolute value exceeds the given value;
(h) producing a PID controlled signal based on the liquid bath temperature difference determined in the step (g); and
(i) inputting the PID controlled signal to means for heating and cooling the liquid bath.

In its preferred embodiments, the present temperature controlling means comprises a cascade control system. The first controller is provided with operation circuits for calculating a timely suitable set point (which varies with time) of temperature of the thermostat in response to the detected temperature (which changes with time) of the fluid sample so that the fluid sample may be effectively heated or cooled by the thermostat, according to the detected temperature of the fluid sample, so as to speedily adjust the temperature of the fluid sample to its desired set point without causing any overshoot or undershooting of the liquid bath temperature relative to the set point temperature of the fluid sample. The first and second operation formulas on which the operation circuits are based are expressed as a function of the difference between the set point temperature of the fluid sample and its detected temperature in view of the afore-mentioned object and the details thereof are experimentally determined according to a thermostat to be used, kind of bath liquid used therefor, a fluid sample container to be immersed in the liquid and so forth. Moreover, the heating and cooling of the thermostat are effectively controlled according to a PID action formed in the second controller.

BRIEF DESCRIPTION OF THE DRAWINGS

FIG. 3($a$) is a flow chart of the routine of a preferred software program for temperature controlling means according to the present invention;

FIG. 3($b$) is a flow chart of a preferred subroutine for use in the routine of FIG. 3($a$);

DESCRIPTION OF A PREFERRED EMBODIMENT

Figure 1:
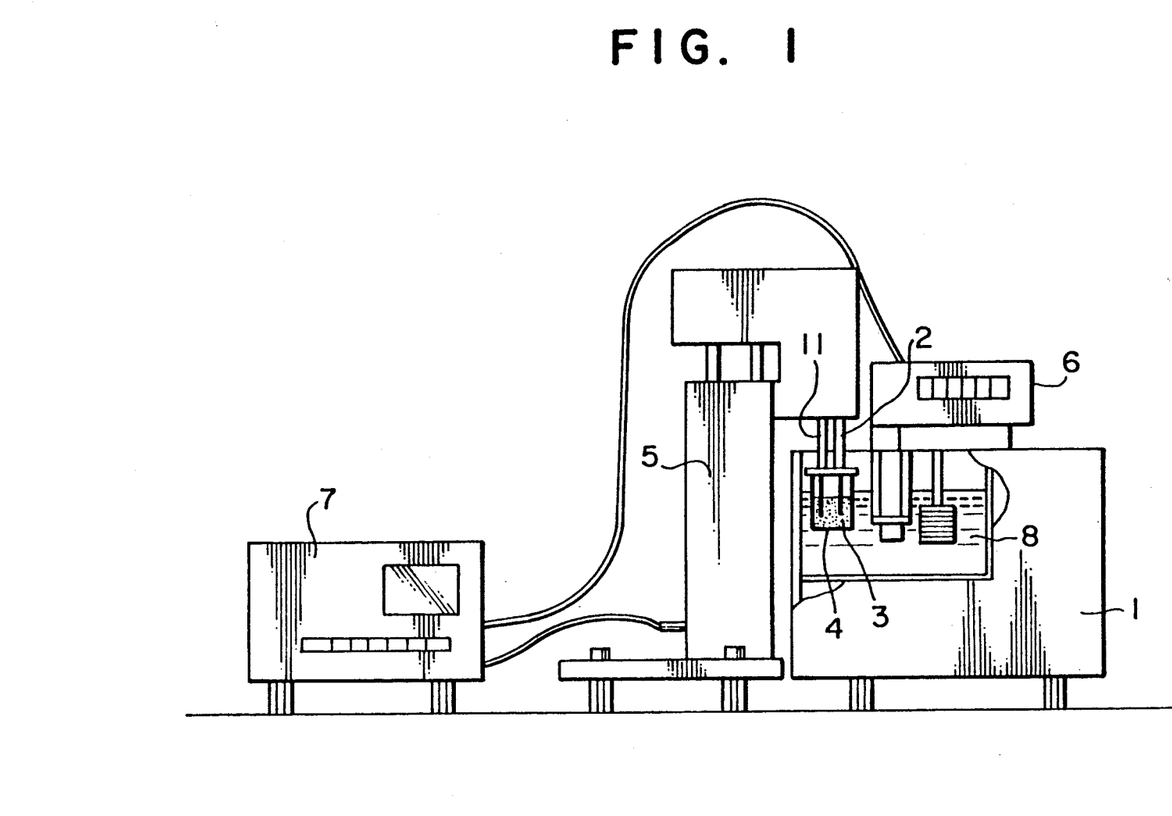
FIG. 1 is an external view of a thermostat for use in viscosity measurement, which is provided with temperature controlling means according to the present invention.

Referring to FIG. 1, a fluid sample 3 whose viscosity is to be measured is received in a sample container 4 and immersed in a liquid bath 8 of a thermostat 1. A viscosity sensor of a viscosity detector 2 and a temperature probe of a first thermometer 11 are immersed in the fluid sample 3, where the viscosity detector 2 and the first thermometer 11 are held by a stand 5. The temperature and viscosity of the fluid sample 3 detected by the detector 2 and the thermometer 11, respectively, are counted and displayed by a recorder 7. The recorder 7 makes an output signal corresponding to the detected temperature of the fluid sample 3 and inputs said signal into a temperature control device 6 of the thermostat 1.

Figure 2:
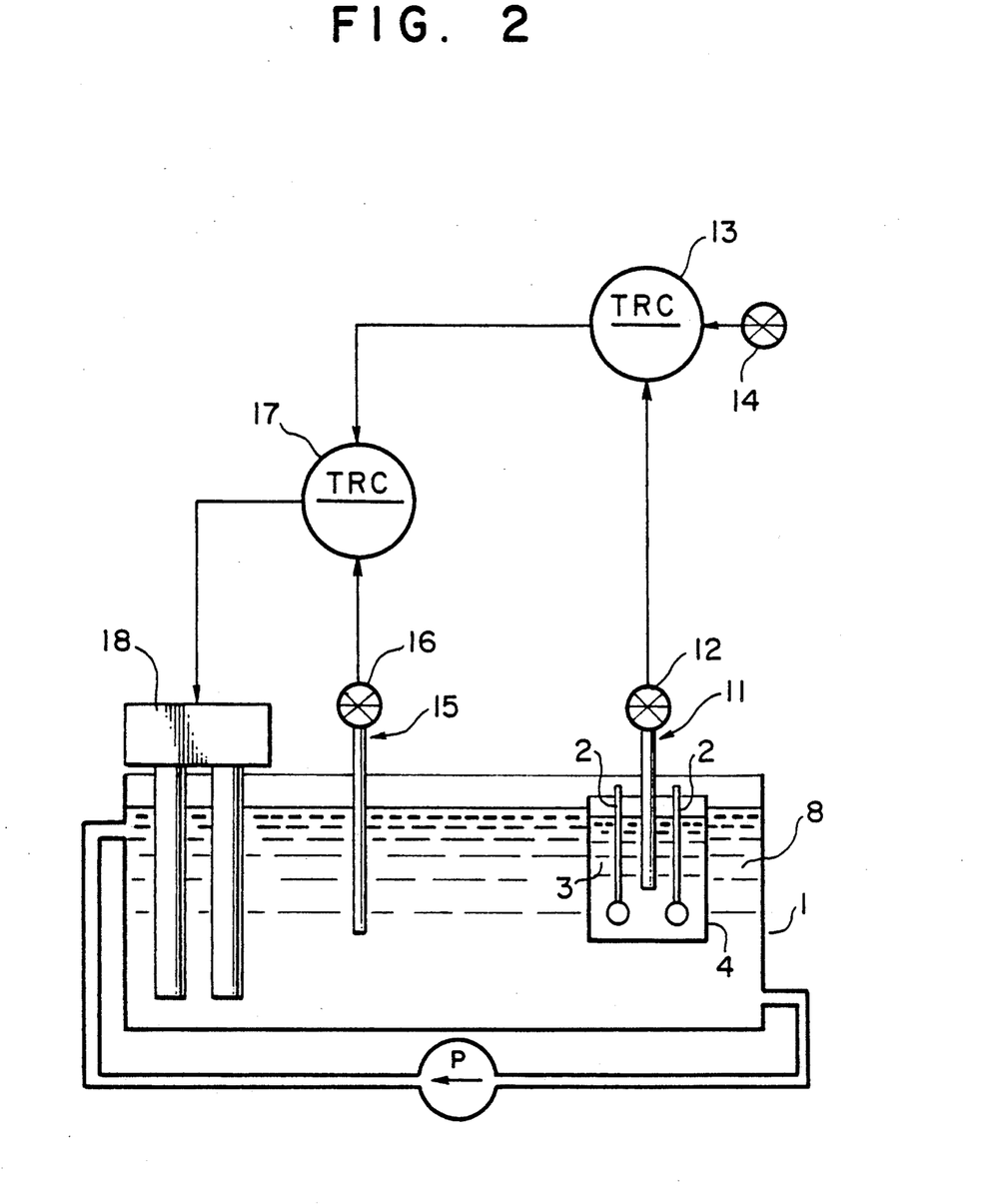
FIG. 2 is an instrumentation flow sheet of temperature controlling means according to the present invention.

The temperature controlling means according to the present invention will be described with reference to FIG. 2. The first thermometer 11 detects the temperature of the fluid sample 3, and a transmitter 12 attached to the first thermometer makes an output signal (hereinafter referred to as a first output signal) corresponding to the detected temperature of the fluid sample 3 and inputs the first output signal into a first controller 13. As the first thermometer 11, a resistance thermometer composed of a platinum resistance wire or a thermistor or a thermocouple thermometer is preferably used. A predetermined set point of temperature of the fluid sample 3 is inputted in advance into the first controller 13 by an inputting means 14. The first controller 13 has two operation circuits which calculate a set point of temperature of the liquid bath 8 according to first and second operation formulas expressed as a function of the difference between the predetermined set point temperature of the fluid sample and the detected value (which changes with time) of the fluid sample temperature. The first and second operation formulas will be described in detail hereinafter. The first controller 13 makes one of the first and second controlled signals corresponding to the respective bath set point temperatures calculated by each of the two operation circuits and inputs the produced controlled signal into a second controller 17. A second thermometer 15 detects the temperature of the liquid bath 8, and a transmitter 16 attached thereto makes an output signal (hereinafter referred to as a second output signal) corresponding to the detected temperature of the liquid bath 8 and inputs the second output signal into the second controller 17. The second controller 17 forms an actuating signal corresponding to the difference in level between the second output signal and the controlled signal inputted thereto and makes a PID controlled signal formed on the basis of the actuating signal for a PID control of operation of heating and cooling means 18. The heating and cooling means 18 heats and cools the liquid bath 8 in response to the PID controlled signal.

It has been found to be preferable, as a result of a lot of experiments, that the aforesaid first and second operation formulas are carried out when the absolute value of the difference between the set point temperature of the fluid sample and its detected temperature exceeds a predetermined value of temperature, e.g., 2 degrees Celsius, and when said absolute value is equal to or less than the predetermined value, respectively. Further, the following general expressions (1) and (2) are preferably used as the first operation formula and the second operation formula, respectively:

$$T_{bS} = T_S + K_p \times (T_S - M_{S(i)}) \quad (1)$$

and $$T_{bS} = T_S + K_p \times (T_S - M_{S(i)}) + \tau \times K_I \times \sum_{j=0}^{i} (T_S - M_{S(j)}) \quad (2)$$

where $T_{bs}$ represents the set point temperature of the liquid bath, $T_s$ the desired set point temperature of the fluid sample, $\tau$ a control period which is defined as the time interval between the successive repetition of determination of the set point temperature of the liquid bath, $M_{S(i)}$ and $M_{S(j)}$ the respective detected temperatures of the fluid sample in the i-th and j-th repetitions, respectively, of the control period after starting the temperature controlling means to operate, $K_p$ a proportional constant, and $K_I$ an integral constant. The values of $K_p$ and $K_I$ are determined from the results of temperature control experiments which have been done upon preselection and preadoption of a thermostat, a bath medium, a fluid sample container and the like to be used. As understood from the above expression, the set point temperature of the liquid bath is changed with variation in the detected temperature of the fluid sample.

Figure 3A:
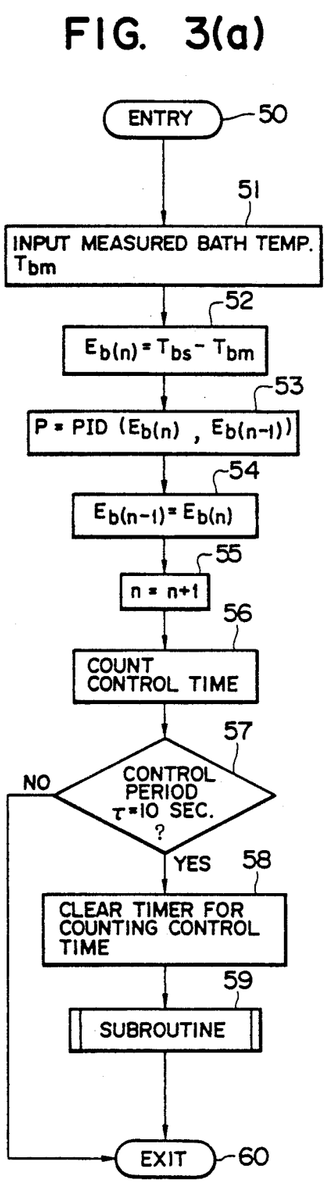
Figure 3B:
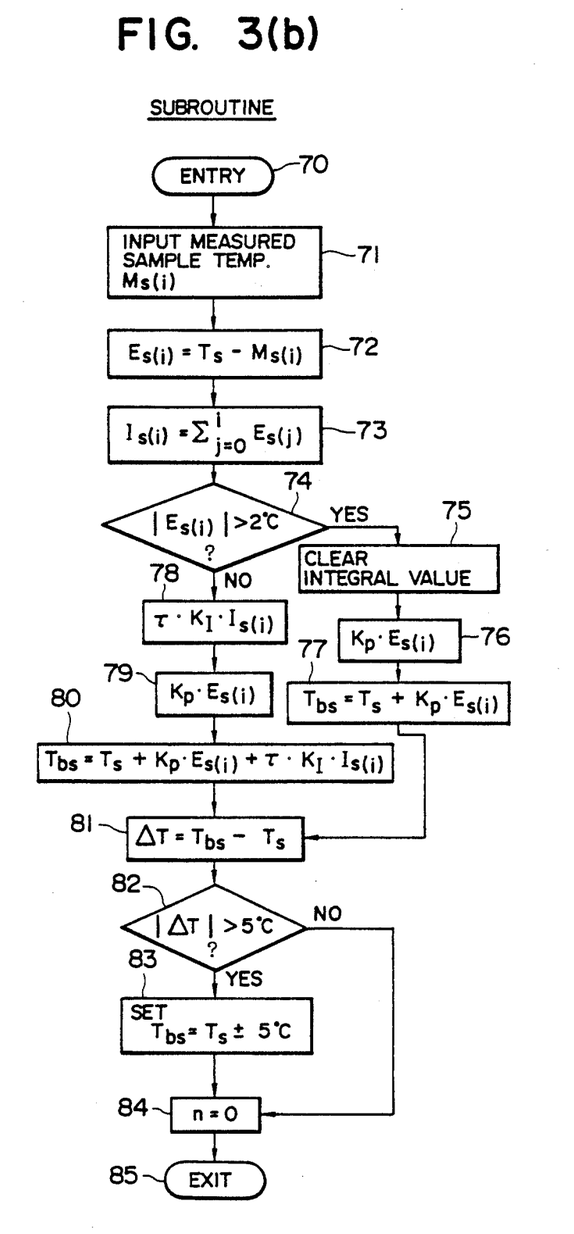

In the present invention, the functions of the first and second controllers are preferably carried out by one microprocessor programmed to provide these functions. The flow chart of a routine for executing these functions is shown in FIGS. 3(a) and 3(b). The program is designed to repeatedly carry out the routine at given equal time intervals.

Referring to FIG. 3(a), each iteration of the routine begins at step 50 and ends at step 60. Hereinafter, in order to briefly describe each step of the routine, the wordings "value of temperature", "set point temperature", "temperature error" and the like are used to mean the respective electric signal levels corresponding to them. At step 51, the measured value $T_{bm}$ of temperature of the liquid bath 8 is provided from the second thermometer 15. At step 52, a liquid bath temperature error $E_{b(n)}$ in the current n-th iteration of the routine is determined by subtracting the value $T_{bm}$ just provided in step 51 from the liquid bath set point temperature $T_{bs}$ which has been determined at steps 80 or 83, described below, in the last (i−1)-th control period. At step 53, using the current liquid bath temperarure error $E_{b(n)}$ just determined in the step 52 and the last liquid bath temperature error $E_{b(n-1)}$ *calculated at step 54 in the previous* (n−1)-th iteration of the routine, a power P is calculated using the PID algorithm. The power P thus obtained is then delivered to the heating and cooling means 18, and the operation of the means 18 is controlled according to the power P. At step 54, the new value of $E_{b(n-1)}$ *is set equal to the value* $E_{b(n)}$ for use in the next (n+1)-th iteration. At step 55, the number n of iteration is incremented by one with a counter. At step 56, a control time, defined as the time elapsed until the number of the iteration reaches n from zero, is counted with a timer. At step 57, the control time is checked whether it is equal to the predetermined control period $\tau$, e.g., 10 seconds, or it is less than $\tau$. If the control time is less than $\tau$, the program skips step 58 and a subroutine 59 the flow chart of which is shown in FIG. 3(b) and exits at step 60. The program repeats the iteration between the steps 50 and 57 until the control time reaches the control period $\tau$, e.g., 10 sec. On the other hand, when the control time is equal to $\tau$, the routine is introduced into step 58. At step 58, after the control time reaches the control period $\tau$, the counting of the control time with the timer is cleared, that is, the timer is set again to zero for use in newly counting the control time in the next set of iterations of the routine. And then the subroutine 59 is entered at step 70, as shown in FIG. 3(b).

Every time when the timer in step 56 counts the control period $\tau$, e.g., 10 sec., the subroutine is carried out. At step 71, the measured value $M_{S(i)}$ of temperature of the fluid sample 3 is provided from the first thermometer 11. At step 72, a fluid sample temperature error $E_{s(i)}$ in the current i-th control period counted at step 56 is determined by subtracting the value $M_{S(i)}$ just provided in step 71 from the sample set point temperature $T_s$ which has been determined by an operator of the controlling system. At step 73 determined is a value $I_{s(i)}$ of integration of the sample temperature errors $E_{s(j)}$ until j is incremented from zero to i, wherein j represents the number of the repetition of the control period. At step 74, the absolute value $|E_{s(i)}|$ of the sample temperature error calculated in step 72 is checked whether or not it is more than a predetermined value of temperature, e.g., 2 degrees Celsius. When the value $|E_{s(i)}|$ exceeds 2 degrees Celsius, the subroutine is introduced into step 75. On the other hand, when it is equal to or less than 2 degrees Celsius, the subroutine is introduced into step 78. At step 75, when the value $|E_{s(i)}|$ exceeds 2 degrees Celsius, the integral value $I_{s(i)}$ obtained in step 73 is cleared. Following step 75, a proportional term $K_p \cdot E_{s(i)}$ is determined at step 76, wherein the constant $K_p$ has been previously determined. At step 77, the bath set point temperature $T_{bs}$ is determined by adding the sample set point temperature $T_s$ to the value of the proportional term determined in step 76 when $|E_{s(i)}|$ is more than 2 degrees Celsius. Then the temperature difference between $T_{bs}$ and $T_s$ is determined at step 81 and compared to a given value of temperature, e.g., 5 degrees Celsius, at step 82. On the other hand, when the value $|E_{s(i)}|$ has proved to be not more than 2 degrees Celsius in step 74, an integral term $\tau \cdot K_I \cdot I_{s(i)}$ is determined at step 78, wherein the constant $K_1$ has been previously determined. Following the step 78, the proportional term $K_p \cdot E_{s(i)}$ is also determined at step 79. At step 80, the bath set point temperature $T_{bs}$ in the current i-th control period is determined by adding the sample set point temperature $T_s$ to the values of the terms determined in steps 78 and 79. At step 81, a temperature difference $\Delta T$ is determined by subtracting the sample set point temperature $T_s$ from the current bath set point temperature $T_{bs}$. At step 82, the absolute value $|\Delta T|$ of said temperature difference is checked whether or not it is more than a predetermined value of temperature, e.g., 5 degrees Celsius. When it exceeds 5 degrees Celsius, the subroutine is introduced into step 82. On the other hand, when it is equal to or less than 5 degrees Celsius, the subroutine is introduced directly into step 84 skipping step 83. At step 83, after the absolute value $|\Delta T|$ has proved to be more than 5 degrees Celsius in the step 81, the new value of $T_{bs}$ is set equal to $(T_s+5)$ or $(T_s-5)$ irrespective of the actual result of calculation of $T_{bs}$ in step 79. On the other hand, when the value $|\Delta T|$ has proved to be 5 degrees Celsius or less in the step 82, the current bath set point temperature $T_{bs}$ remains as it has the value determined in the step 80. Such selective action is taken for avoiding any undesirable overshoot or undershooting of the liquid bath temperature $T_{bm}$ relative to the sample set point tempeature $T_s$ in a transient state of the temperature control of the thermostat 1. At step 84, the counter for counting the number n of iteration of the routine is set to zero. Then the subroutine exits at step 85 and the routine now exits at step 60.

As shown in FIG. 3(b) and described above, when the sample temperature error determined in step 72 is, for example, more than +2 degrees Celsius or less than −2 degrees Celsius, the program skips the steps 78–80 and instead carries out the steps 75–77 and 81. Such selective procedure is provided for effectively controlling the heating and cooling means 18 through the second controller to heat or cool the liquid bath 8 so that the fluid sample temperature can relatively rapidly approach the sample set point temperature.

Figure 4:
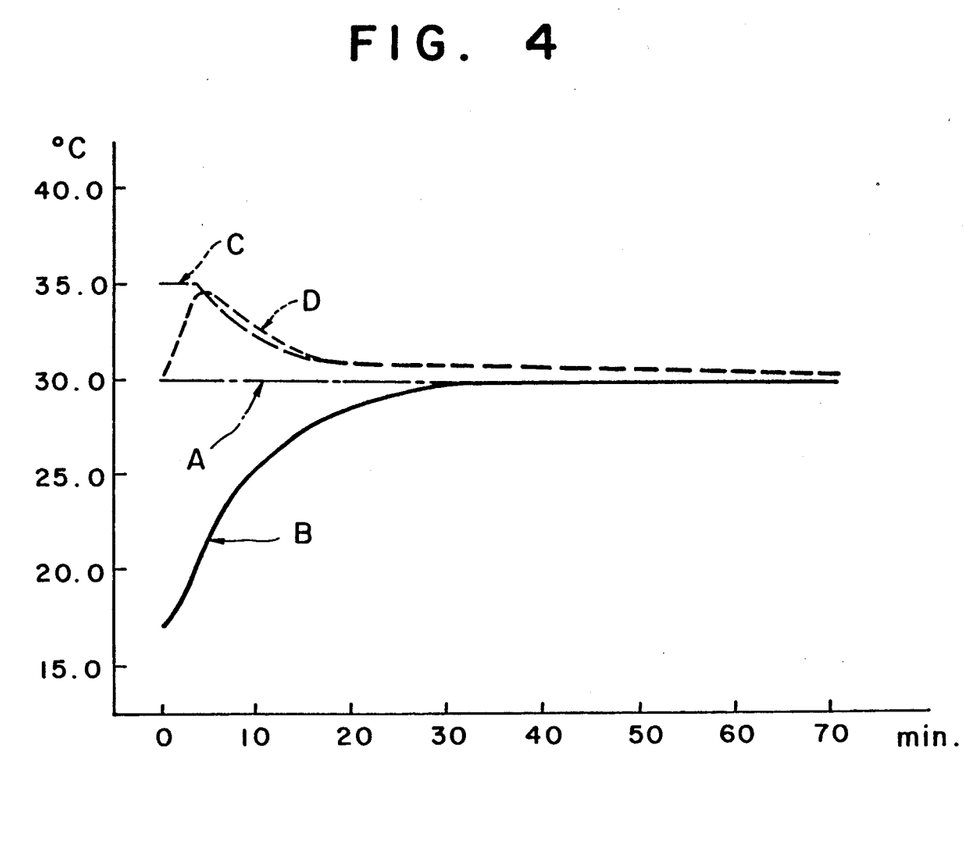
FIG. 4 is a graph of an experimental result of controlling the temperatures of a liquid bath and a fluid sample according to the present invention.
Figure 5:
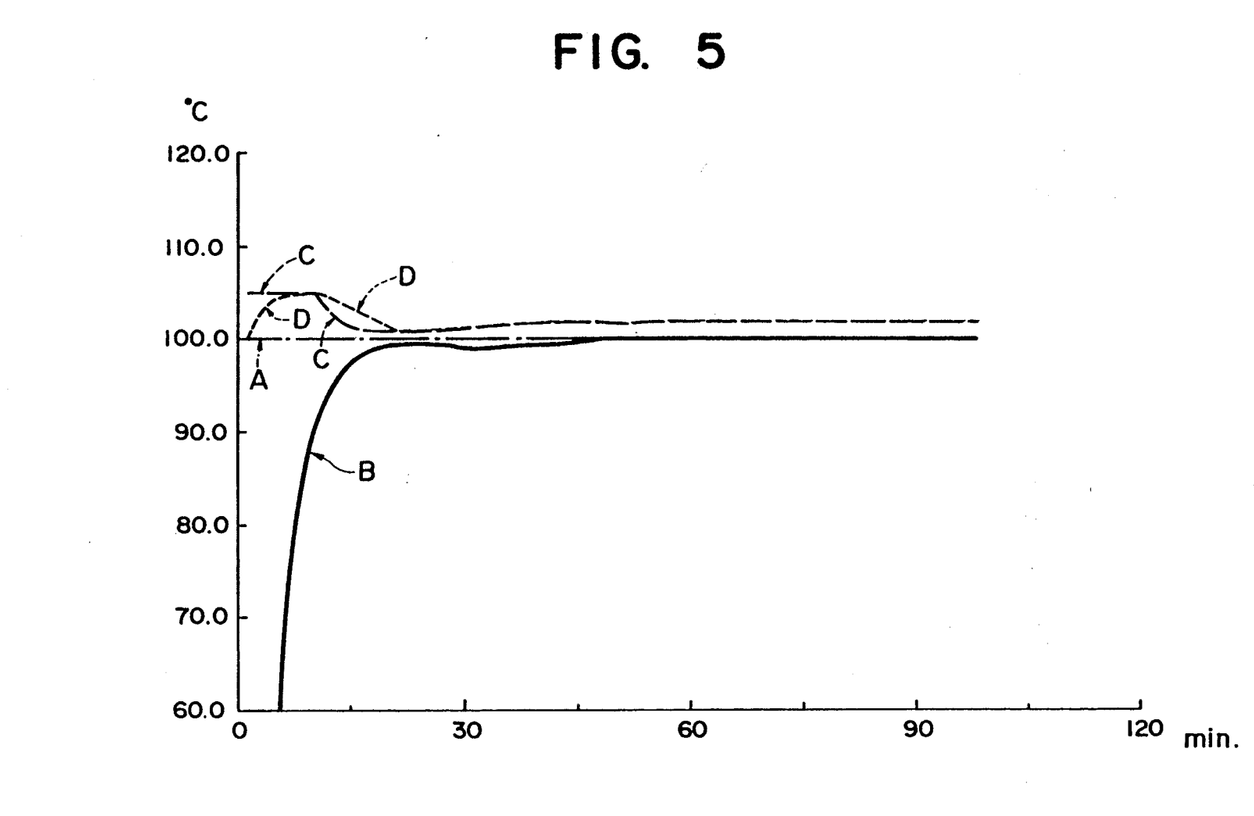
FIGS. 5 and 6 are graphs of another two experimental results of controlling the temperatures of a liquid bath and a fluid sample according to the present invention.
Figure 6:
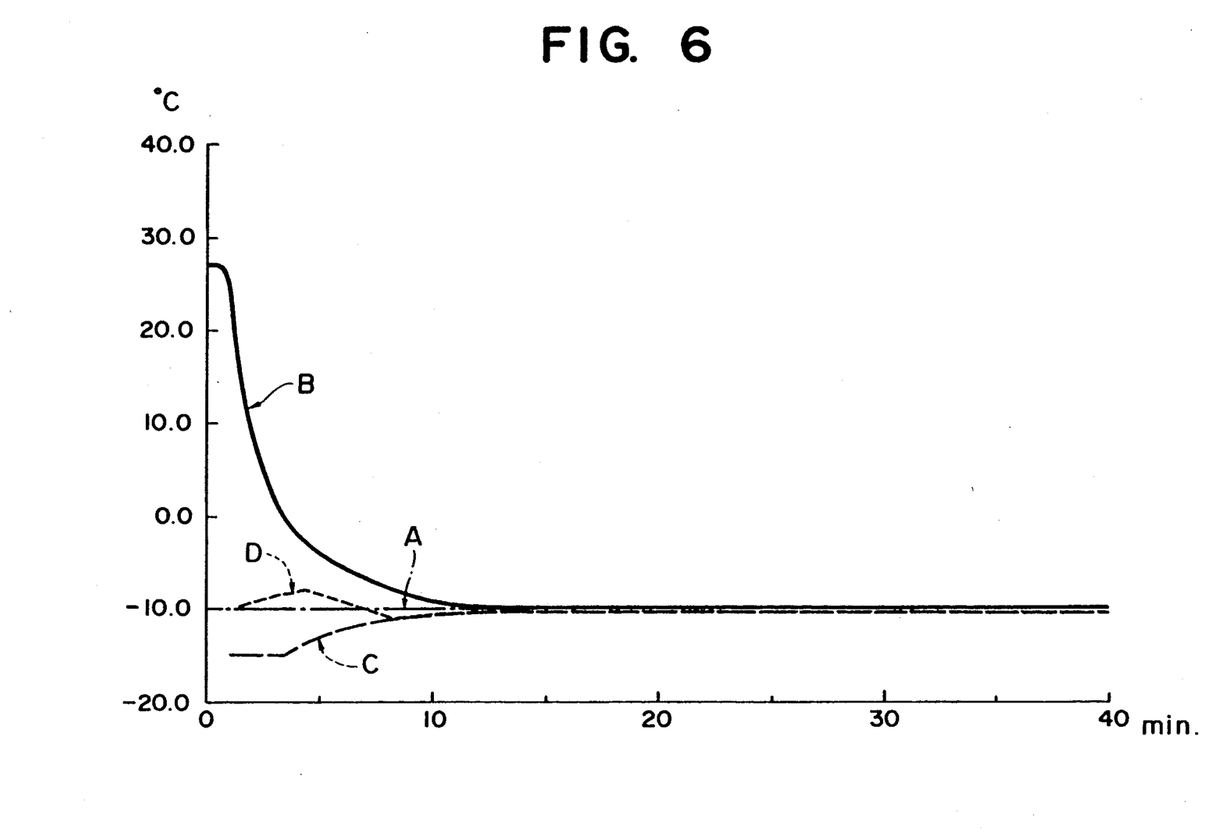

Next, results of temperature control experiments carried out using the temperature controlling means according to the present invention will be described with reference to FIGS. 4 to 6. In FIGS. 4 to 6, A designates the set point temperature of a fluid sample, B denotes the detected temperature of the fluid sample, C the set point temperature of a liquid bath, calculated by the aforementioned first controller, and D the detected temperature of the liquid bath. These temperatures A to D were pursued by a computer. As shown in FIG. 4, the temperature B of the fluid sample which is an oil liquid having a relatively high viscosity is adjusted to its set point A of 30 degrees Celsius after about 35 minutes and then kept constant. FIGS. 5 and 6 show experimental results obtained by using fluid samples which have a low viscosity and a high heat conductivity relative to those of the fluid sample used in the experiment the result of which is shown in FIG. 4. As shown in FIGS. 4 to 7, in an initial stage of the respective experiments, the set point temperature C of the liquid bath is adjusted to be higher or lower by 5 degrees Celsius than the corresponding set point temperature of the fluid sample according to the temperature controlling program as shown in FIG. 3(b).

Figure 7:
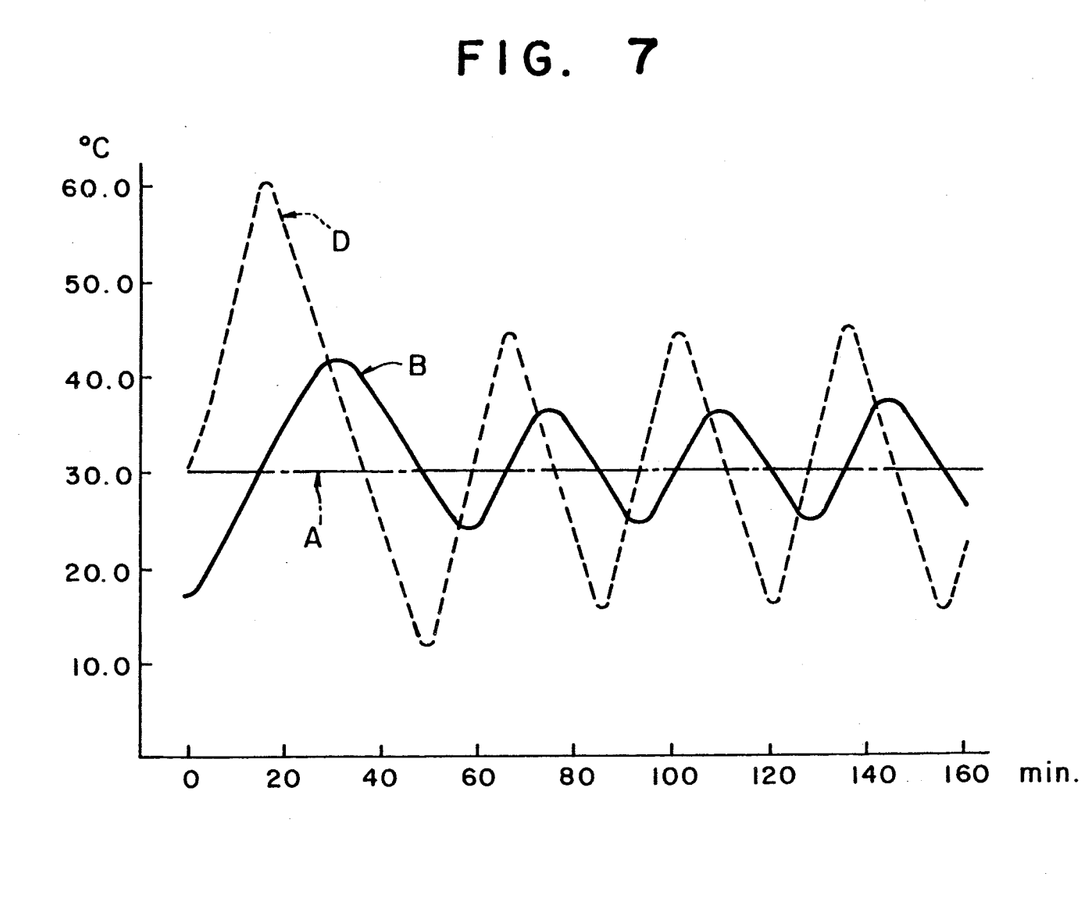
FIG. 7 is a graph of an experimental result of heating and cooling the medium bath under the conditions that the set point and the detected value of temperature of the fluid sample are directly fed back to a second controller in the present temperature controlling means without using a first controller in the present temperature controlling means.

FIG. 7 shows an experimental result when the operation of the heating and cooling means 18 is controlled according to a PID controlled signal formed on the basis of the difference between the set point temperature of a fluid sample and its detected temperature, in the second controller 17. In this experiment, the first controller 13 is not used, and the signals corresponding to the set point temperature of the fluid sample and its detected temperature are directly inputted into the second controller 17, where the detected temperature of a liquid bath is not fed back to the second controller 17. As shown in FIG. 7, the temperature D of the liquid bath repeatedly considerably fluctuates with time, and thereby the temperature B of the fluid sample also waves with a considerable delay of response and does not approach its set point even after a long time.

What is claimed is:

1. Temperature controlling means for controlling the temperature of a fluid sample immersed in a liquid bath, comprising:

first means for detecting the temperature of the fluid sample and producing a first output signal corresponding thereto;

a first controller for receiving the first output signal and an input command corresponding to a desired set point of temperature of the fluid sample, determining a set point of temperature of the liquid bath according to one of first and second operation formulas expressed as a function of the difference between the desired set point temperature of the fluid sample and its detected temperature and producing one of first and second controlled signals corresponding to the respective liquid bath set point temperatures determined by carrying out the first operation formula and the second operation formula;

second means for checking the difference between the set point temperature of the fluid sample and its detected temperature and whether or not the absolute value of the difference exceeds a predetermined value of temperature and performing the first operation formula when the absolute value exceeds the predetermined value and performing the second operation formula when the absolute value is at most equal to the predetermined value;

third means for limiting either of the levels of the first and second controlled signals relative to the level of the input command corresponding to the fluid sample set point temperature, the fourth means being operative to determine a temperature error by subtracting the fluid sample set point temperature from the determined set point temperature of the liquid bath, to check the temperature error and whether or not the absolute value of the temperature error exceeds a given value of temperature and to set the new value of the liquid bath set point temperature equal to the sum of the fluid sample set point temperature and the given value when the temperature error exceeds the given value and equal to the value of the fluid sample set point temperature minus the given value when the temperature error is less than the negative quantity of the given value;

fourth means for detecting the temperature of the liquid bath and producing a second output signal corresponding thereto;

heating and cooling means for heating and cooling the liquid bath; and a second controller for receiving the second output signal and one of the first and second controlled signals the levels of which have been limited by the third means, forming an actuating signal corresponding to the difference in level between the received one of the first and second controlled signals and the second output signal and subsequently inputting to the heating and cooling means a PID controlled signal formed on the basis of the actuating signal, the heating and cooling means being operative to heat and cool the liquid bath according to the PID controlled signal inputted thereto.

2. Temperature controlling means according to claim 1, wherein the first controller includes means for performing the first operation formula which is defined as follows:

$$T_{bs} = T_s + K_p \times (T_s - M_{s(i)})$$

wherein:
- $T_{bs}$ = the set point temperature of the liquid bath;
- $T_s$ = the set point temperature of the fluid sample;
- $M_{s(i)}$ = the detected temperature of the fluid sample in the
- i-th repetion of a control period; and
- $K_p$ = proportional constant.

3. Temperature controlling means according to claim 1, wherein the first controller includes means for performing the second operation formula which is defined as follows:

$$T_{bS} = T_S + K_p \times (T_S - M_{S(i)}) + \tau \times K_I \times \sum_{j=0}^{i} (T_S - M_{S(j)})$$

wherein:
- $T_{bs}$ = the set point temperature of the liquid bath;
- $T_s$ = the set point temperature of the fluid sample;
- $\tau$ = control period which is defined as the time interval between the succesive repetitions of determination of $T_{bs}$;
- $M_{s(i)}$ and $M_{s(j)}$ are the detected temperatures of the fluid sample in the i-th repetition and in the j-th repetition, respectively, of the control period $\tau$;
- $K_p$ = proportional constant; and
- $K_I$ = integral constant.

4. Temperature controlling means according to claim 1, wherein the predetermined value of temperature for the second means is equal to 2 degrees Celsius.

5. Temperature controlling means according to claim 1, wherein the given value of temperature for the third means is equal to 5 degrees Celsius.

6. A temperature controlling means according to claim 3, wherein the control period is equal to 10 seconds.

7. A method of controlling the temperature of a fluid sample immersed in a liquid bath, comprising the steps of
(a) measuring the temperature of the fluid sample;
(b) determining the fluid sample temperature difference between a desired set point temperature of the fluid sample and its measured temperature;
(c) determining a set point temperature of the liquid bath according to one of first and second operation formulas expressed as a function of the fluid sample temperature difference, the first and second operation formulas being carried out when the absolute value of the fluid sample temperature difference exceeds a predetermined value of temperature and when said absolute value is within the predetermined value, respectively;
(d) determining the set point temperature difference between the determined set point temperature of the liquid bath and the set point temperature of the fluid sample;
(e) setting the new value of the set point temperature of the liquid bath equal to the sum of the fluid sample set point temperature and a given value of temperature when the set point temperature difference is more than the given value, and equal to the value of the fluid sample set point temperature minus the given value when the set point temperature difference is less than the negative quantity of the given value;
(f) measuring the temperature of the liquid bath;
(g) determining the liquid bath temperature difference between the set point temperature of the liquid bath and its measured temperature, where the value of the liquid bath set point temperature is equal to the one determined in the step (c) when the absolute value of the set point temperature difference is within the given value and is equal to one of the new values set in the step (e) when said absolute value exceeds the given value;
(h) producing a PID controlled signal based on the liquid bath temperature difference determined in the step (g); and
(i) inputting the PID controlled signal to means for heating and cooling the liquid bath.

8. A method according to claim 7, wherein the set point temperature of the liquid bath is determined by performing the first operation formula which is defined as follows:

$$T_{bs} = T_s + K_p \times (T_s - M_{s(i)})$$

wherein:
- $T_{bs}$ = the set point temperature of the liquid bath;
- $T_s$ = the set point temperature of the fluid sample;
- $M_{s(i)}$ = the detected temperature of the fluid sample in the
- i-th repetition of a control period; and
- $K_p$ = proportional constant.

9. A method according to claim 7, wherein the set point temperature of the liquid bath is determined by performing the second operation formula which is defined as follows:

$$T_{bS} = T_S + K_p \times (T_S - M_{S(i)}) + \tau \times K_I \times \sum_{j=0}^{i} (T_S - M_{S(j)})$$

wherein:
- $T_{bs}$ = the set point temperature of the liquid bath;
- $T_s$ = the set point temperature of the fluid sample;
- $\tau$ = control period which is defined as the time interval between the successive repetitions of determination of T;
- $M_{s(i)}$ and $M_{s(j)}$ are the detected temperatures of the fluid sample in the i-th repetition and in the j-th repetition, respectively, of the control period $\tau$;
- $K_p$ = proportional constant; and
- $K_I$ = integral constant.

10. A method according to claim 7, wherein the predetermined value of temperature in the step (c) is equal to 2 degrees Celsius.

11. A method according to claim 7, wherein the given value of temperature in the step (e) is equal to 5 degrees Celsius.

12. A method according to claim 9, wherein the control period is equal to 10 seconds.

13. A method of controlling the temperature of a fluid sample in a liquid bath, comprising the steps of:
 (a) measuring the temperature of a fluid sample in a liquid bath;
 (b) determining the difference between a desired sample temperature and the measured sample temperature;
 (c) determining a desired bath temperature according to a first function of the difference determined in step (b) when the absolute value of the difference determined in step (b) is greater than a predetermined value and according to a second function of the difference determined in step (b) when the absolute value of the difference determined in step (b) is not greater than the predetermined value;
 (d) determining the difference between the desired bath temperature and the desired sample temperature;
 (e) limiting the desired bath temperature determined in step (c) to the desired sample temperature plus a given value when the difference determined in step (d) is greater than said given value and to the desired sample temperature minus said given value when the difference determined in step (d) is less than the negative of said given value;
 (f) measuring the bath temperature;
 (g) determining the difference between the desired bath temperature from step (e) and the measured bath temperature; and (h) heating or cooling the liquid bath as a function of the difference determined in step (g) to effect a difference of zero.

14. The method according to claim 13, wherein steps (a)–(h) are repeated a plurality of times.

15. The method according to claim 14, wherein the first function is defined by $$T_{bs} = T_s + K_p \times (T_s - M_{s(i)})$$

wherein:
 $T_{bs}$ = the desired temperature of the liquid bath;
 $T_s$ = the desired temperature of the fluid sample;
 $M_{s(i)}$ = the measured temperature of the fluid sample in the i-th repetition; and
 $K_p$ = proportional constant.

16. The method according to claim 14, wherein the temperature of the liquid bath is determined by performing the second function is defined by:

$$T_{bS} = T_S + K_p \times (T_S - M_{S(i)}) + \tau \times K_I \times \sum_{j=0}^{i} (T_S - M_{S(j)})$$

wherein:
 $T_{bs}$ = the desired temperature of the liquid bath;
 $T_s$ = the desired temperature of the fluid sample;
 $\tau$ = a control period defined as the time interval between the successive repetitions of determination of $T_{bs}$; $M_{s(i)}$ and $M_{s(j)}$ are the measured temperatures of the fluid sample in the i-th repetition and in the j-th repetition, respectively, of the control period $\tau$;
 $K_p$ = proportional constant; and
 $K_I$ = intergral constant.

17. The method according to claim 13, wherein the predetermined value in step (c) is equal to 2 degrees Celsius.

18. The method according to claim 13, wherein the given value of temperature in step (e) is equal to 5 degrees Celsius.

19. The method according to claim 16, wherein the control period is equal to 10 seconds.

20. A device for controlling the temperature of a fluid sample in a liquid bath, comprising:
 (a) first means for measuring the temperature of a fluid sample in a liquid bath;
 (b) second means for determining the difference between a desired sample temperature and the measured sample temperature;
 (c) third means for determining a desired bath temperature according to a first function of the difference determined by said second means when the absolute value of the difference determined by said second means is greater than a predetermined value and according to a second function of the difference determined by said second means when the absolute value of the difference determined by said second means is not greater than the predetermined value;
 (d) fourth means for determining the difference between the desired bath temperature and the desired sample temperature;
 (e) fifth means for limiting the desired bath temperature determined by said third means to the desired sample temperature plus a given value when the difference determined by said fourth means is greater than said given value and to the desired sample temperature minus said given value when the difference determined by said fourth means is less than the negative of said given value;
 (f) sixth means for measuring the bath temperature;
 (g) seventh means for determining the difference between the desired bath temperature from said third means and said fifth means and the measured bath temperature; and
 (h) means for heating or cooling the liquid bath as a function of the difference determined by the seventh means to effect a difference of zero.

21. The device according to claim 20, further comprising means for periodically repeating the functions of means (a)–(h).

22. The device according to claim 21, wherein the first function comprises:

$$T_{bs} = T_s + K_p \times (T_s - M_{s(i)})$$

wherein:
 $T_{bs}$ = the desired temperature of the liquid bath;
 $T_s$ = the desired temperature of the fluid sample;
 $M_{s(i)}$ = the measured temperature of the fluid sample in the i-th repetition; and
 $K_p$ = proportional constant.

23. The device according to claim 21, wherein the second function comprises:

$$T_{bS} = T_S + K_p \times (T_S - M_{S(i)}) + \tau \times K_I \times \sum_{j=0}^{i} (T_S - M_{S(j)})$$

wherein:
$T_{bs}$ = the desired temperature of the liquid bath;
$T_s$ = the desired temperature of the fluid sample;
$\tau$ = a control period defined as the time interval between the successive repetitions of determination of $T_{bs}$; $M_{S(i)}$ and $M_{S(j)}$ are the measured temperatures of the fluid sample in the i-th repetition and in the j-th repetition, respectively, of the control period $\tau$;
$K_p$ = proportional constant; and
$K_I$ = integral constant.

24. The device according to claim 20, wherein the predetermined value of temperature for the third means is equal to 2 degrees Celsius.

25. The device according to claim 20, wherein the given value of temperature for the fifth means is equal to 5 degrees Celsius.

26. The device according to claim 23, wherein the control period is equal to 10 seconds.

* * * * *